United States Patent [19]

Seto et al.

[11] Patent Number: 5,026,922
[45] Date of Patent: Jun. 25, 1991

[54] PROCESS FOR PREPARING CLYCOL ALDEHYDE

[75] Inventors: Takatoshi Seto, Ami; Takashi Yokoi, Shiga; Masaki Odagiri; Makoto Imanari, both of Ami, all of Japan

[73] Assignee: Research Association for Utilization of Light Oil, Tokyo, Japan

[21] Appl. No.: 455,147

[22] Filed: Dec. 22, 1989

[30] Foreign Application Priority Data

Dec. 27, 1988 [JP] Japan .................. 63-329850

[51] Int. Cl.$^5$ .................. C07C 45/29; C07C 45/32
[52] U.S. Cl. .................. 568/486; 568/471; 568/485
[58] Field of Search .................. 568/471, 486, 485

[56] References Cited

U.S. PATENT DOCUMENTS

| 4,503,261 | 3/1985 | Sauer et al. | 568/471 |
| 4,511,739 | 4/1985 | Sauer et al. | 568/471 |
| 4,555,583 | 11/1985 | Toyoda et al. | 568/471 |
| 4,814,513 | 3/1989 | Graf et al. | 568/471 |

FOREIGN PATENT DOCUMENTS

| 0217280 | 4/1987 | European Pat. Off. . | |
| 3037536 | 5/1982 | Fed. Rep. of Germany . | |
| 3535483 | 4/1987 | Fed. Rep. of Germany . | |
| 0046237 | 3/1984 | Japan | 568/471 |
| 61-69740 | 4/1986 | Japan . | |
| 62-45548 | 2/1987 | Japan . | |
| 2045548 | 2/1987 | Japan | 568/486 |
| 168281 | 11/1965 | U.S.S.R. . | |
| 8400955 | 3/1984 | World Int. Prop. O. | 568/471 |

OTHER PUBLICATIONS

Patent Abstracts of Japan, vol. 10, No. 235, Aug. 1986 (Res. Assoc. Util of Lieght Oil).

Primary Examiner—Werren B. Lone
Attorney, Agent, or Firm—Oblon, Spivak, McClelland, Maier & Neustadt

[57] ABSTRACT

There is disclosed a process for preparing glycol aldehyde from ethylene glycol by use of a complex system catalyst comprising copper and other inorganic component, which comprises permitting 0.001 to 0.3 mole of oxygen per one mole of ethylene glycol to be copresent in the reaction system.

13 Claims, No Drawings

PROCESS FOR PREPARING GLYCOL ALDEHYDE

BACKGROUND OF THE INVENTION

This invention relates to a process for preparing glycol aldehyde, particularly to a process for preparing glycol aldehyde from ethylene glycol by use of a complex system catalyst comprising copper and other inorganic component.

Glycol aldehyde is a useful compound as the starting material for α-amino acids, pharmaceuticals, agricultural chemicals, chemicals for photography or special polymers, etc. and also as fiber treating agents, odorants and deodorants.

Primary known techniques for preparing glycol aldehyde from ethylene glycol are shown below.

(1) Process which comprises contacting ethylene glycol with a copper-chromium system catalyst at 300° to 400° C. together with hydrogen and steam (U.S.S.R. Patent No. 168281, 1965).

(2) Process which comprises contacting ethylene glycol with a copper-zinc alloy (brass) at 220° to 370° C. under a reduced pressure of 10 to 45 mmHg (Masato Nomura, Yoshito Fujiwara, Research Report No. 15 of Faculty of Engineering, Kinki University).

(3) Process which obtains glycol aldehyde by oxidative dehydrogenation of ethylene glycol with the use of a metal catalyst of silver, copper or gold (German OLS DE 3535483 A1).

In the above method (1), there is the problem that selectivity of glycol aldehyde is low and no glycol aldehyde can be obtained with good efficiency.

In the above method (2), the reaction system must be maintained under high reduced pressure as 10 to 45 mmHg, and moreover the liquid hourly space velocity (LHSV) must be made extremely small as 0.01/hr, whereby production efficiency is remarkably poor.

The above method (3) is a method in which glycol aldehyde is obtained by oxidative dehydrogenation as shown below by the formula (1) by using a single metal as the catalyst and introducing oxygen in an amount of 0.5 to 1.5-fold mole which is the theoretical amount or more based on ethylene glycol, but glyoxal, etc. are by-produced in large amounts and selectivity is poor.

$$HOC_2H_4OH + \tfrac{1}{2}O_2 \rightarrow HOCH_2CHO + H_2O \quad (1)$$

Thus, for preparation of glycol aldehyde of high purity with good efficiency, none of the known techniques can be said to be industrially satisfactory.

Also, the process for producing glycol aldehyde from ethylene glycol by use of a copper system catalyst has a great problem of lowering in catalyst activity.

SUMMARY OF THE INVENTION

Thus, an object of the present invention is to provide a process for preparing glycol aldehyde with good efficiency, and a process for preparing glycol aldehyde stably without lowering in catalyst activity.

The present inventors have studied intensively in order to solve the above problems of the prior art, and consequently found that the activity deterioration of the catalyst can be markedly improved by introducing a minute amount of oxygen into the reaction system during the reaction with high glycol aldehyde selectivity with a complex system catalyst such as copper-zinc oxide catalyst, etc., thereby enabling stable preparation of glycol aldehyde with good efficiency.

More specifically, the present invention is a process for preparing glycol aldehyde from ethylene glycol by use of a complex system catalyst comprising copper and other inorganic component, which comprises permitting 0.001 to 0.3 mole of oxygen per one mole of ethylene glycol to be co-present in the reaction system.

DESCRIPTION OF THE PREFERRED EMBODIMENTS

(1) Catalyst

The "complex system catalyst of copper and other inorganic component" which can be used in the present invention means one comprising a combination of copper or copper oxide as the active main component and other inorganic oxide or metal, including mixed catalysts or carried copper catalysts.

The "other inorganic oxide or metal" herein mentioned means a material which aids catalytic functions of copper or copper oxide which is main active component of the catalyst physically or chemically, and they may include, for example, alkali metal oxides such as zinc oxide, chromium oxide, manganese oxide, cadmium oxide, cesium oxide, etc.; alkaline earth metal oxides such as barium oxide, etc.; alumina, silica, thoria, pumice, diatomaceous earth, asbestos, zinc, palladium, cadmium, cobalt, ruthenium; or combination of these.

As the mixed catalyst, for example, oxides of Cu-Zn, oxides of Cu-Cr, oxides of Cu-Mn, oxides of Cu-Mg, or oxides of Cu-Cd, etc. can be included. Also, these further combined with other components can be used as the catalyst.

As the carried copper catalyst, catalysts having copper oxide or the above-mentioned complex system catalyst, etc. carried on pumice, diatomaceous earth, alumina, silica, asbestos, thoria, etc. can be included. As the catalyst which can be used in the present invention, those as mentioned above are not limitative. These catalysts can be prepared according to known methods.

As a compositional amount of the catalyst other than Cu-Zn oxide system catalyst, copper component is preferably contained in an amount of 1 to 70%, particularly 5 to 60% in terms of copper oxide based on the total weight of the catalyst.

Among these, the Cu-Zn oxide system catalyst is preferred. In this case, a preferred composition comprises a ratio corresponding to 0.3 to 3 parts by weight of zinc as zinc oxide per one part by weight of copper as calculated on copper oxide.

In the case of the Cu-Zn oxide catalyst, it can be prepared according to the method in which a Cu-Zn alloy shaped in powder, fiber, yarn or net is heated in the presence of oxygen, the method in which a mixture of a copper salt such as copper nitrate, copper acetate, etc. and a zinc salt such as zinc nitrate, zinc acetate, etc. is calcined, or the method in which an alkali is added into a solution of nitrates of copper and zinc and the co-precipitate salt obtained is calcined, etc. The calcination temperature of the copper-zinc system catalyst at this time may be 500° to 1200° C., and particularly when calcined at high temperature, the glycol aldehyde selectivity during the reaction tends to become higher preferably. In this case, hydrogen reduction is effected at a temperature of about 150° to 300° C. before use for the reaction, but since the catalyst is reduced rapidly at the initial stage of the reaction, no hydrogen reduction treatment may be effected.

(2) Reaction Conditions

In the present invention, by introducing ethylene glycol, water and, in addition thereto, a minute amount of oxygen into a reactor filled with the catalyst as described above, glycol aldehyde can be produced stably for a long time.

An amount of water added may be generally 0.1 to 100 mole, preferably 0.5 to 50 mole, particularly preferably 1 to 10 mole, per one mole of ethylene glycol. If water is less than 0.1 mole, the selectivity of glycol aldehyde will be undesirably lowered. If water exceeds 100 mole, the space time yield is poor to lower economy.

Oxygen is introduced as molecular oxygen, and, generally, it is preferred in cost to introduce it as air. An amount of oxygen added is generally 0.001 to 0.3 mole, preferably 0.005 to 0.2 mole per one mole of ethylene glycol. If the oxygen amount is less than 0.001 mole, deterioration of catalyst activity is great, while on the other hand, if the amount of oxygen added is large, glyoxal and carbon dioxide are by-produced in large amounts, whereby glycol aldehyde selectivity will be lowered.

In the method of the above-mentioned known German OLS DE 3535483 A1, oxygen is similarly introduced into the reaction system 8, but in this method, copper single metal is used as the catalyst, and as shown in the above formula (1), the so-called oxidative dehydrogenation reaction is carried out which liberates the hydrogen of ethylene glycol with oxygen as water, whereby the amount of oxygen added is required to be the theoretical amount or larger, namely as large as 0.5 to 1.5-fold moles, relative to ethylene glycol. In contrast, in the present invention, by using primarily a complex system oxide catalyst of copper and introducing a minute amount of 0.001 to 0.3-fold mole relative to ethylene glycol, activation deterioration is markedly improved. Its mechanism may be probably considered to be due to the fact that the redox state of copper during the reaction is stabilized by introduction of a minute amount of oxygen.

A reaction temperature may be generally 180° to 400° C., preferably 200° to 350° C., particularly preferably 240° to 290° C. At a temperature lower than 180° C., conversion of ethylene glycol is low, while if it exceeds 400° C., selectivity of glycol aldehyde will be lowered.

LHSV may be generally 0.05 to 20/hr, preferably about 0.1 to 10/hr.

A reaction pressure may be either normal, reduced or pressurized. In view of economy of the reaction device, easiness in running, normal pressure may be preferably used.

As an atmospheric gas, in addition to ethylene glycol, steam and air, an inert gas such as nitrogen, argon, etc. may be also added.

The present invention is described in more detail by referring to Examples.

In the following experimental examples, analysis of the product was carried out by use of gas chromatography and high performance liquid chromatography. Conversion of ethylene glycol and selectivity of glycol aldehyde were calculated on the basis of the following formulae.

$$\text{Conversion (\%)} = \frac{\text{Amount of ethylene glycol consumed by the reaction (mole)}}{\text{Amount of ethylene glycol charged (mole)}} \times 100$$

$$\text{Selectivity (\%)} = \frac{\text{Amount of glycol aldehyde formed (mole)}}{\text{Amount of ethylene glycol consumed by the reaction (mole)}} \times 100$$

EXAMPLE 1

A catalyst obtained by calcining a catalyst precursor having an average particle size of 2 mm, a composition comprising 50 parts by weight of CuO and 45 parts by weight of ZnO and a specific surface area of 31 m²/g (manufactured by Nikki Kagaku K. K., N-211) at 1000° C. for 4 hours was filled in a reaction tower made of stainless steel with an inner diameter of 15 mm in an amount corresponding to an apparent volume of 10 ml.

Through the filled tower was first passed steam at 200° C. at LHSV: 0.5/hr for one hour, and then hydrogen diluted with nitrogen at 300° C., GHSV: 600/hr for 2 hours, to obtain a copper-zinc oxide system catalyst.

Next, while maintaining the reaction tower at 270° C., a mixture of ethylene glycol:water = 1:6 (molar ratio) was gasified through a preheater, passed at LHSV: 5/hr and at the same time air containing 0.02 mole of oxygen per one mole of ethylene glycol was passed. Ethylene glycol conversion after 10 hours was found to be 25%, and glycol aldehyde selectivity 86%. Ethylene glycol conversion after 110 hours was 23%, and glycol aldehyde selectivity 83%.

EXAMPLE 2

The powder obtained by pulverizing the N-211 catalyst manufactured by Nikki Kagaku K. K. used in Example 1 was added to a small amount of deionized water, stirred into a slurry, which was added with α-alumina (SA-5218, manufactured by Norton Co., spherical size 5 mm) and stirred slowly to have the α-alumina impregnated with the N-211 powder, followed by drying and calcination in air at 1000° C. for 4 hours, to give a CuO-ZnO-α-Al$_2$O$_3$ catalyst (CuO/ZnO weight ratio = 50/45, CuO-ZnO carried ratio = 14% by weight).

The catalyst was filled into a reaction tower made of stainless steel with an inner diameter of 15 mm in an amount of 37.5 mm in apparent volume and 46.4 g in weight, and then the reaction pretreatment was completed similarly as in Example 1 by passing first steam at 200° C. at LHSV: 0.5/hr for one hour, and then hydrogen diluted with nitrogen at 300° C., GHSV: 600/hr for 2 hours.

Next, while maintaining the reaction tower at 257° C., a mixture of ethylene glycol:water = 1:6 (molar ratio) was gasified through a preheater, passed at LHSV: 0.7/hr and at the same time the reaction was practiced for a long time in the form of passing air containing 0.09 mole of oxygen per one mole of ethylene glycol. However, during the reaction, 200 hours, 400 hours and 600 hours, respectively, from the reaction initiation time, introduction of ethylene glycol and water was stopped for one hour.

The change in catalyst activity is shown in Table 1. As is apparent from the Table, good reaction results could be obtained stably for a long time.

TABLE 1

| Reaction time (hr) | Results of reaction | |
|---|---|---|
| | Conversion of ethylene glycol (%) | Selectivity of glycol aldehyde (%) |
| 100 | 26 | 87 |
| 300 | 23 | 88 |
| 500 | 24 | 81 |
| 700 | 20 | 81 |

EXAMPLE 3

The experiment was carried out in the same manner as in Example 1 except for changing the catalyst precursor to one having a composition comprising 70 parts by weight of CuO and 25 parts by weight of ZnO. Ethylene glycol conversion after 10 hours was found to be 27%, and glycol aldehyde selectivity 85%. Ethylene glycol conversion after 110 hours was found to be 25%, and glycol aldehyde selectivity 82%.

EXAMPLE 4

The experiment was carried out in entirely the same manner as in Example 1 except for changing the molar ratio of ethylene glycol and water introduced into the reaction system to 1:8. As the result, ethylene glycol conversion after 10 hours was found to be 27%, and glycol aldehyde selectivity 89%. Ethylene glycol conversion after 110 hours was found to be 26%, and glycol aldehyde selectivity 85%.

COMPARATIVE EXAMPLE 1

The experiment was carried out in entirely the same manner as in Example 1 except for feeding no air containing 0.02 mole of oxygen per mole of ethylene glycol into the reaction system. Ethylene glycol conversion after 10 hours was found to be 22% and glycol aldehyde selectivity 74%, but ethylene glycol conversion was lowered to 9% after 110 hours, with the glycol aldehyde selectivity being 85%.

COMPARATIVE EXAMPLE 2

The experiment was carried out in entirely the same manner as in Example 2 except for feeding no air containing 0.09 mole of oxygen per mole of ethylene glycol into the reaction system. Ethylene glycol conversion after 2 hours was found to be 20% and glycol aldehyde selectivity 73%, but ethylene glycol conversion was lowered to 9% after 20 hours, with the glycol aldehyde selectivity being 82%.

COMPARATIVE EXAMPLE 3

The experiment was carried out in entirely the same manner as in Example 2 except for charging the amount of oxygen introduced into the reaction system as air to 0.5 mole per one mole of ethylene glycol. Ethylene glycol conversion after 2 hours was found to be 35% and glycol aldehyde selectivity 37%. A large quantity of by-products such as carbon dioxide, glyoxal and formic acid etc., were detected.

According to the present invention, in preparing glycol aldehyde from ethylene glycol, by using a complex system catalyst of copper and other inorganic component and introducing a minute amount of molecular oxygen into the reaction system, substantially no lowering in catalyst activity with lapse of time is seen and yet selectivity of glycol aldehyde can be maintained at high level as such. Therefore, glycol aldehyde of high purity can be produced by continuous running over a long term without exchange of the catalyst or reactivation treatment.

We claim:

1. A highly selective and long lived catalytic process for preparing glycol aldehyde from ethylene glycol which comprises allowing ethylene glycol to be in contact with a copper-containing catalyst in the presence of 0.001 to 0.3 mole of oxygen per mole of ethylene glycol at a temperature in the range of about 180° to 400° C.

2. A process according to claim 1, wherein an amount of oxygen co-present is 0.005 to 0.2 mole per one mole of ethylene glycol.

3. A process according to claim 1, wherein the process is carried out by introducing ethylene glycol, water and oxygen into a reactor filled with the complex system catalyst.

4. A process according to claim 3, wherein an amount of water is 0.1 to 100 mole per one mole of ethylene glycol.

5. A process according to claim 4, wherein an amount of water is 0.5 to 50 mole per one mole of ethylene glycol.

6. A process according to claim 1, wherein a reaction temperature is 200° to 350° C.

7. A process according to claim 6, wherein a reaction temperature is 240° to 290° C.

8. A process according to claim 1, wherein a liquid hourly space velocity of a reaction is 0.05 to 20/hr.

9. A process according to claim 8, wherein a liquid hourly space velocity of a reaction is 0.1 to 10/hr.

10. A process according to claim 1, wherein the copper-containing catalyst comprises a combination of copper or copper oxide as an active main component and another inorganic oxide or metal selected from the group consisting of mixed catalysts and carried copper catalysts.

11. A process according to claim 10, wherein the mixed catalyst is selected from the group consisting of oxides of Cu-Zn oxides of Cu-Cr, oxides of Cu-Mn, oxides of Cu-Mg and oxides of Cu-Cd.

12. A process according to claim 10, wherein the carried copper catalyst comprises copper oxide carried on pumice, diatomaceous earth, alumina, silica, asbestos or thoria.

13. A process according to claim 1, wherein the catalyst is a copper-zinc system catalyst containing 0.3 to 3 parts by weight of zinc as zinc oxide per 1 part by weight of copper as calculated on copper oxide.

* * * * *